United States Patent
Ball et al.

(10) Patent No.: US 7,011,686 B2
(45) Date of Patent: *Mar. 14, 2006

(54) REVERSE-TYPE HUMERAL PROSTHESIS

(75) Inventors: Robert J. Ball, Winona Lake, IN (US); Jeffrey M. Ondrla, Leesburg, IN (US); Anne-Céline Godest, Lyons (FR)

(73) Assignee: DePuy Products, Inc., Warsaw, IN (US)

(*) Notice: Subject to any disclaimer, the term of this patent is extended or adjusted under 35 U.S.C. 154(b) by 2 days.

This patent is subject to a terminal disclaimer.

(21) Appl. No.: 10/260,992

(22) Filed: Sep. 30, 2002

(65) Prior Publication Data

US 2004/0064190 A1    Apr. 1, 2004

(51) Int. Cl.
 *A61F 2/40* (2006.01)
(52) U.S. Cl. ............................ 623/19.14
(58) Field of Classification Search ......... 623/19.11, 623/19.12, 19.13, 19.14
See application file for complete search history.

(56) References Cited

U.S. PATENT DOCUMENTS

| | | | |
|---|---|---|---|
| 3,842,442 A | | 10/1974 | Kolbel |
| 3,869,730 A | * | 3/1975 | Skobel ................. 623/19.12 |
| 3,916,451 A | | 11/1975 | Buechel et al. |
| 3,978,528 A | | 9/1976 | Crep |
| 4,003,095 A | | 1/1977 | Gristina |
| 4,206,517 A | | 6/1980 | Pappas et al. |
| 4,693,723 A | | 9/1987 | Gabard |
| 5,163,961 A | * | 11/1992 | Harwin ...................... 623/23 |
| 5,261,914 A | | 11/1993 | Warren |
| 5,425,779 A | | 6/1995 | Schlosser |
| 5,462,563 A | | 10/1995 | Shearer et al. |
| 5,702,457 A | | 12/1997 | Walch et al. |
| 5,723,018 A | | 3/1998 | Cyprien et al. |
| 5,741,335 A | | 4/1998 | Gerber et al. |
| 5,984,927 A | | 11/1999 | Wenstrom, Jr. et al. |
| 6,206,925 B1 | | 3/2001 | Tornier |
| 6,228,120 B1 | | 5/2001 | Leonard et al. |
| 6,475,243 B1 | * | 11/2002 | Sheldon et al. .......... 623/22.28 |
| 6,736,851 B1 | * | 5/2004 | Maroney et al. ......... 623/19.12 |
| 6,790,234 B1 | * | 9/2004 | Frankle .................... 623/19.12 |

FOREIGN PATENT DOCUMENTS

| | | |
|---|---|---|
| EP | 0 299 889 | 1/1989 |
| EP | 0 712 617 A1 | 5/1996 |
| EP | 0 715 836 | 6/1996 |
| EP | 0 903 128 | 3/1999 |
| EP | 0 927 548 | 7/1999 |
| EP | 1 195 149 | 4/2002 |
| FR | 2 652 498 | 4/1991 |
| FR | 2 699 400 | 6/1994 |
| WO | WO 99/49792 | 3/1999 |
| WO | WO 99/65413 | 6/1999 |
| WO | WO 00/41653 | 7/2000 |
| WO | WO 02/39931 | 5/2002 |
| WO | WO 02/39933 A1 * | 5/2002 |

* cited by examiner

*Primary Examiner*—Corrine McDermott
*Assistant Examiner*—Thomas J. Sweet
(74) *Attorney, Agent, or Firm*—Maginot, Moore & Beck (57) ABSTRACT

A humeral component of a shoulder prosthesis includes a stem configured for implantation within the humerus. A reverse articulating component is mounted to the stem by a connection mechanism. The reverse component defines a substantially concave bearing surface. The bearing surface is part of a bearing member that is engaged to a support member that is associated with the connection mechanism. A kit is provided which includes differently configured bearing members and support members to allow intraoperative selection and assembly of an optimum articulating component.

28 Claims, 4 Drawing Sheets

REVERSE-TYPE HUMERAL PROSTHESIS

BACKGROUND OF INVENTION

The present invention relates generally to prosthetic joints, and more particularly to a shoulder prosthesis. The invention has specific application with respect to the humeral component of the shoulder prosthesis.

Conventional prostheses for the replacement of the shoulder joint include a segment engaged within the humerus bone and a mating articulating segment associated with the glenoid bone. In the typical shoulder prosthesis, the upper portion of the humerus is replaced by a unitary structure. This structure includes a stem designed to extend downwardly into a bore or cavity formed within the humerus. This stem is secured within the bone by bone cement or through the use of coatings configured to promote bone ingrowth to secure the stem in place. Again with the conventional prosthesis, the stem is attached to a body portion that is designed to replace portions of the humerus at the anatomical neck of the bone. A generally spherical head portion projects from a surface of the body. This spherical head mates with a complementary concave articulating component mounted within the glenoid.

In recent years, modular shoulder prostheses have been developed to account for the different anatomies of the shoulder joint among patients. For instance, differently sized prostheses are necessary to accommodate the different bone sizes of prospective patients. Similarly, different shoulder joints may require different angles of inclination of the articulating elements relative to the long axis of the humerus bone. Thus, a variety of modular prostheses have been developed that permit substitution of particular components of the prosthesis as necessary prior to implantation.

One problem faced by both the conventional and the modular shoulder prostheses is the deterioration of the shoulder joint that can accompany a shoulder arthroplasty. For instance, a patient who has undergone shoulder arthroplasty may experience loss of soft tissue and soft tissue strength, which can eventually lead to a total loss of key constraints that maintain the patency of the joint. This loss of soft tissue and soft tissue strength can allow unnatural joint loads to be produced, which can compromise the function of the prosthetic joint and/or lead to joint pain.

One solution for this problem is revision of the shoulder prosthesis. This revision can entail the substitution of different articulating components, or differently sized prosthetic components. In one treatment, the shoulder prosthesis is changed to a "reverse" type prosthesis. A typical prosthetic shoulder replicates the current anatomy of the joint. Specifically, the humeral component provides a convex articular surface, much like the natural end of the humerus. This convex surface mates with a concave glenoid component. A "reverse" type prosthesis essentially reverses the arrangement of the articulating surfaces. Specifically, the glenoid component includes a convex or partially spherical component, while the complementary concave surface is integrated into the humeral implants.

One consideration involved in the use of a reverse prosthesis is that the concave articular surface, that is now part of the humeral component, may actually protrude into the metaphyseal region of the humerus. This modified geometry can require modification of the metaphyseal portion of the bone as well as the prosthesis.

In order to address these needs, prior systems have required total revision of the joint. A total revision entails removal of the entire implant, including the stem that is fixed within the diaphyseal portion of the humerus. Of course, this surgical procedure is very difficult and invasive, and can place the patient and the shoulder joint at risk.

SUMMARY OF THE INVENTION

The invention contemplates a humeral component for a shoulder prosthesis that comprises a stem configured for implantation within the humerus bone, the stem including a proximal portion configured for positioning in the metaphysis of the humerus. The humeral component also comprises an articulating component including a support member and a bearing member removably mounted within the support member and defining a substantially concave articulating surface. A connection mechanism is provided for connecting the articulating component to the proximal portion of the stem. In a preferred embodiment, the connection mechanism is configured to permit connection of the articulating component at variable angles relative to the stem.

In one feature of the invention, the articulating component is mounted to the implanted stem so that the component is not engaged within the bone. In a preferred embodiment, the articulating component is situated outside the prepared end of the humerus. In an alternative embodiment, portions of the articulating component can reside within the envelop of the proximal end of the bone without being engaged to the component. Thus, the articulating component can be readily removed and replaced without disturbing the bone. This approach can be particularly useful in a trial procedure.

In one aspect of the invention, a kit can be provided which includes a plurality of differently configured support members and differently configured bearing members. The differently configured components can be combined to provide a reverse articulating element that is ideally suited for the patient's anatomy and that optimally emulates the original natural shoulder joint of the patient.

In certain embodiments, the support member defines an axis, and the connection mechanism is configured to connect the support member along that axis. The concave bearing surface can then adopt different orientations relative to that axis. For example, the bearing surface can define a central axis projecting from the centroid of the concave surface, in which the central axis is substantially aligned with the axis of the support member. Alternatively, the central axis can be laterally offset, angularly offset, or both, relative to the axis of the support member. These different reverse concave surface orientations can be produced by differences in the bearing member or differences in the support member.

In one preferred feature of the invention, the support member defines a cavity and the bearing member includes a body sized to fit within the cavity. The cavity of the support member and the body of the bearing member can define snap-fit features therebetween. For example, the snap-fit features can include a circumferential rim defined on the body and a complementary circumferential recess defined in the cavity. The snap-fit feature can also be accomplished by a snap-ring and groove arrangement in which both components are provided with a groove. Alternatively, the cavity of the support member and the body of the bearing member define a press-fit engagement therebetween.

In certain embodiments, the cavity and the body can also define an anti-rotation feature therebetween to prevent relative rotation between the support member and the bearing member. In other embodiments, the bearing member and support member can be connected to permit relative rotation between the two components about an axis projecting from the articulating surface of the bearing member.

The present invention contemplates a surgical procedure in which the stem of the humeral component is implanted within a humerus. The support member of the reverse articulating component can be mounted to the proximal end of the stem by way of the connection mechanism. The orientation of the articulating component can be fixed relative to the stem to produce an optimum prosthetic joint.

In some circumstances, a convex articulating element may be initially provided. In a revision procedure or during the initial shoulder arthroplasty procedure, the convex element can be removed and replaced with a reverse articulating component of the present invention. The component, or more specifically its bearing member and support member, can be selected from among a plurality of differently configured members to produce an artificial humeral joint implant that best fits the current anatomy of the patient.

It is one object of the invention to provide a humeral implant that can be readily altered based on the conditions of the patient's shoulder. Another object is to provide such a humeral implant that can be easily modified during an initial shoulder arthroplasty procedure or in a revision surgery. These and other objects and benefits will become apparent upon consideration of the following written description, along with the accompanying figures.

DESCRIPTION OF THE PREFERRED EMBODIMENTS

For the purposes of promoting an understanding of the principles of the invention, references will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the inventions as would normally occur to one skilled in the art to which this invention pertains.

Figures 1, 2, 3:
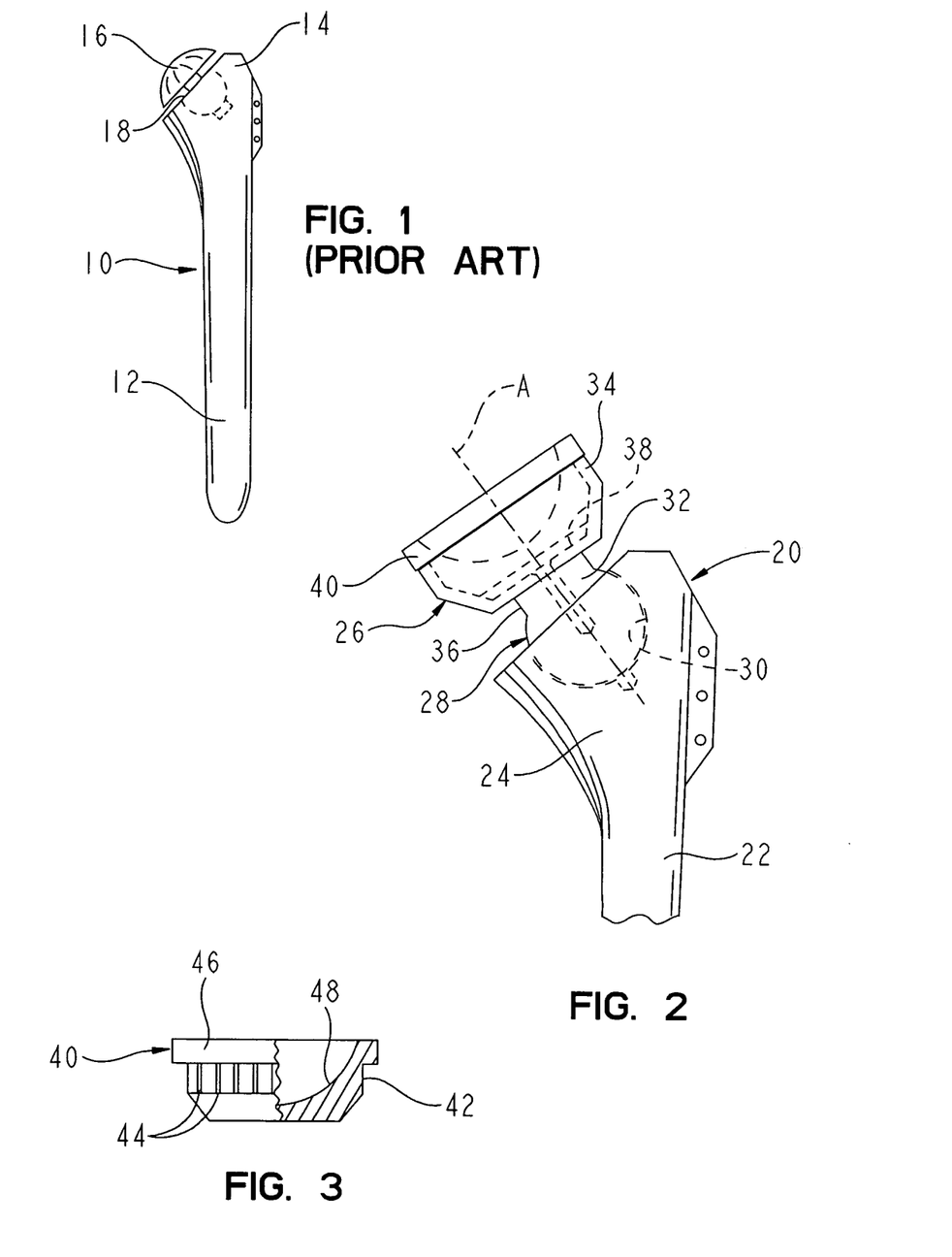
FIG. 1 is side elevational view of a humeral component of a shoulder prosthesis in accordance one prior art system.
FIG. 2 is a side elevational partial view of a humeral component of a shoulder prosthesis in accordance with one embodiment of the present invention.
FIG. 3 is a side view of a bearing member of the reverse prosthesis shown in FIG. 2.

The context of the present invention can be understood with reference to a humeral component of a shoulder prosthesis of the prior art. For instance, a humeral implant 10, as shown in FIG. 1, can include a stem 12 configured to be implanted within a bore prepared in the humerus bone. The proximal portion 14 of the stem is at the prepared proximal end of the bone. The proximal portion supports a prosthetic humeral head 16 by way of a connection mechanism 18.

In this type of prior implant, the humeral implant carries a convex surface, such as the semi-spherical prosthetic head 16. A complementary concave surface is supported by the glenoid. However, in some instances, difficulties arise in the shoulder anatomy of the patient, such as deterioration of the adjacent soft tissue, which makes the typical humeral component, such as the implant 10 shown in FIG. 1, problematic.

In order to address those circumstances, the present invention contemplates a "reverse-type" humeral implant. A reverse-type implant incorporates the concave surface of the humeral component, rather than the component supported by the glenoid. As a consequence, the convex bearing surface is carried by the glenoid. One embodiment of the present invention contemplates a humeral implant 20 as shown in FIG. 2. The implant 20 can include a stem 22 that is configured similar to known stems, such as stem 12 shown in FIG. 1. Specifically, the stem 22 is configured to be implanted in a bore prepared in the humerus bone. The stem can be implanted by way of a bone cement or can include a prepared surface that encourages or enhances bone ingrowth.

The proximal portion 24 of the stem 22 resides in the proximal or metaphyseal portion of the humerus bone. Typically, the proximal portion 24 is flared outwardly to emulate the increased cross sectional area of the humerus at its proximal end. In accordance with this embodiment of the invention, the proximal portion 24 supports an articulating component 26 by way of a universal connection mechanism 28. In accordance with one aspect of the invention, the articulating component is a reverse-type component.

The universal connection mechanism 28 can be configured to permit three-dimensional orientation of the reverse component 26 relative to the proximal portion 24 of the stem. More specifically, the universal connection mechanism 28 allows the reverse component to be oriented at an angle relative to the longitudinal axis of the humerus that is dictated by the anatomy of the patient's natural shoulder. The object, of course, is for the resulting shoulder prosthesis to accurately replicate the movement of the patient's natural shoulder. In accordance with one specific embodiment, the universal connection mechanism 28 can constitute a socket 30 defined in the proximal portion 24 of stem 22. A ball element 32 is connected to the reverse component 26. The ball is configured for articulating bearing movement within the socket 30. Means can be provided within the ball and socket arrangement to fix the two components relative to each other.

In accordance with one aspect of the invention, the reverse component 26 can include a support cup 34 that can be connected to the ball element 32 by way of a post 36. In one embodiment, the support cup 34, post 36 and ball element 32 are integrally formed. In an alternative embodiment, the post is integral with either the ball element or the support cup, and a fixation element is used to connect the two components together.

The support cup 34 defines a recess 38 for receiving a bearing member 40 therein. With reference to FIG. 3, it can be seen that the bearing member in accordance with one embodiment of the present invention constitutes an insert body 42 that fits within the recess 38 of the support cup 34. Preferably, the insert body 42 includes a plurality of anti-rotation features 44 that can be in the form of circumferentially spaced ribs. These ribs can fit within corresponding complementary features defined in the recess 38. Alternatively or in addition, both the insert body 42 and the anti-rotation features 44 can form a press-fit engagement with the recess 38.

The bearing member 40 includes a circumferential rim 46 that fits or bears against the proximal edge of the support cup 34. The bearing member 40 further defines an articulating surface 48 that is concave, in the form of the reverse-type component contemplated for the present invention.

In accordance with one feature of the invention, the bearing member 40 allows for a variety of geometries for the articulating surface 48. In the illustrated embodiment of FIGS. 2 and 3, the surface 48 is generally spherical and is symmetrically positioned around the positioning axis A (see FIG. 2) of the reverse component 26. Moreover, the shape of the articulating surface 48 can be modified from the spherical shape shown in FIG. 3.

An alternative embodiment of the invention is shown in FIGS. 4–10. A humeral implant 50 includes a stem 52, that can be similar to the stem 22 described above. The stem 52 includes a proximal portion 54 that can also be similar to the corresponding proximal portion 24 of the stem 22. However, in accordance with the preferred features of this embodiment, the proximal portion 54 includes angulation relief portions 54A and 54B at the medial and lateral aspects, respectively, of the proximal portion. These relief portions 54a, 54b represent areas of the proximal portion 24, shown in dashed lines in FIG. 4, that are removed from the proximal portion 54 of the humeral implant 50. These relief portions allow for different angular positions of an articulating component 56, as described in more detail herein.

Figure 4:
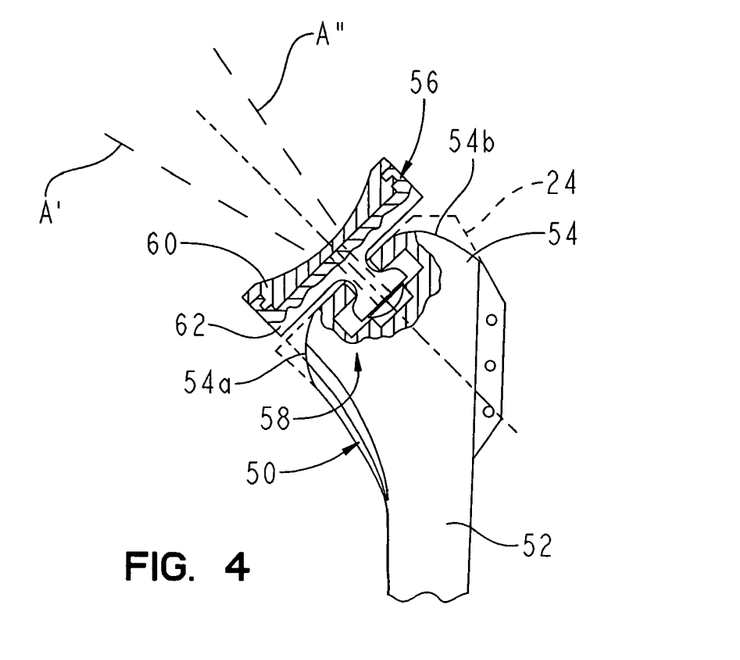
FIG. 4 is side partial cross-sectional view of the humeral component of a shoulder prosthesis in accordance with a further embodiment of the present invention.

As with the previous embodiment, the articulating component 56 is a reverse-type component. The component 56 is connected to the stem 52 by way of an adjustable connection mechanism 58. Preferably, the adjustable connection mechanism permits three-dimensional movement and orientation of the reverse component 56 relative to the stem 52, and ultimately the humerus bone. As explained above, the adjustable connection mechanism 58 can allow fine tuning of the position of the reverse component 56 relative to the complementary glenoid component of the shoulder prosthesis. This optimum orientation can be determined intra-operatively or can be predetermined and verified by pre-surgery x-rays demonstrating the anatomy of the patient's natural shoulder.

Figure 5:
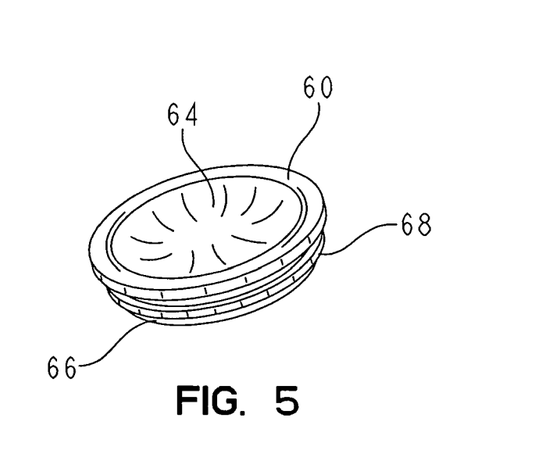
FIG. 5 is a perspective view of the bearing member of the humeral component shown in FIG. 4.
Figure 6:
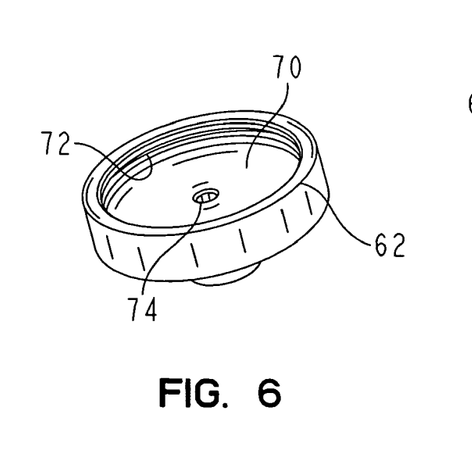
FIG. 6 is a bearing support of the humeral component shown in FIG. 4.

As shown in more detail in FIGS. 5 and 6, the reverse component 56 includes a bearing member 60 (FIG. 5) mounted on a bearing support 62 (FIG. 6). The bearing member 60 defines a bearing or articulating surface 64 that corresponds to the articulating surface 48 of the bearing member 40 of the previous embodiment. The bearing surface 64 is configured to mate with a corresponding convex surface associated with the glenoid component of the shoulder prosthesis.

In the preferred illustrated embodiment, the bearing member 60 includes a hub 66 projecting below the bearing surface 64. A circumferential engagement rib 68 can be defined along the length of the hub 66, as shown in FIG. 5. The bearing support 62 then defines a cavity 70 that is sized to receive the hub 66 of the bearing member 60. In addition, the cavity 70 defines a circumferential engagement recess 72 that is configured to receive the engagement rib 68 of the bearing member 60. In one aspect of the invention, engagement rib 68 and hub 66 can be configured for a snap-fit engagement within the corresponding recess 72 and cavity 70. In addition, the hub cavity can incorporate press-fit features, such as mating Morse tapers.

In accordance with the preferred embodiment, the two members of the reverse component 56, namely the bearing member 60 and the bearing support 62, can be formed of a biocompatible, but strong, material. The bearing support 62 can be a metal, while the bearing member 60 can be formed of a non-metallic material that provides a smooth and long-life articulating bearing surface. Preferably, the engagement ribs 68 of the bearing member 60 is formed of a material that can be slightly deformed to allow the rib to be snapped through the cavity 70 and into the engagement recess 72 of the bearing support 62.

As indicated above, the reverse component 56 is mounted to the stem 52 of the humeral implant 50 by way of an adjustable connection mechanism 58. The adjustable connection mechanism can take on a variety of forms that permit varying degrees of positional adjustment of the reverse component relative to the stem. In the preferred embodiment, the adjustable connection mechanism 58 allows the reverse component 56 to be aligned at a wide range of conical angles relative to the stem 52. One specific adjustable connection mechanism 58 is shown in detail in FIG. 7. In particular, the proximal portion 54 of the stem 52 can define an adjustment cavity 80. A clamping member 82 is slidably disposed within the cavity 80. An adjustment screw 84 is threadedly engaged with the clamping member 82. The adjustment screw 84 can include an internal drive feature that allows the screw to be extended into contact with the cavity 80 once the appropriate position of the reverse component 56 has been accomplished. As the adjustment screw is driven into contact with the cavity, it tends to push the clamping member 82 upward and also into contact with the cavity.

The clamping member 82 and the bearing support 62 can incorporate a press-fit interface 86 to allow the two components to be engaged together. Alternatively, the clamping member 82 can be integrally formed with the bearing support 62. However, in the embodiment illustrated in FIG. 7, a Morse-taper provides the press-fit interface 86 between the two components. In order to allow access to the adjustment screw 84, the bearing support 62 defines an access opening 74, shown in FIGS. 6 and 7. Thus, a driving tool can be passed through the access opening 74 to engage the screw 84. Once the position of the reverse component 56 has been established, the screw 84 can be tightened to push the screw 84 and the clamping member 82 into clamping engagement with the wall of the adjustment cavity 80.

Figures 7, 8, 9, 10:
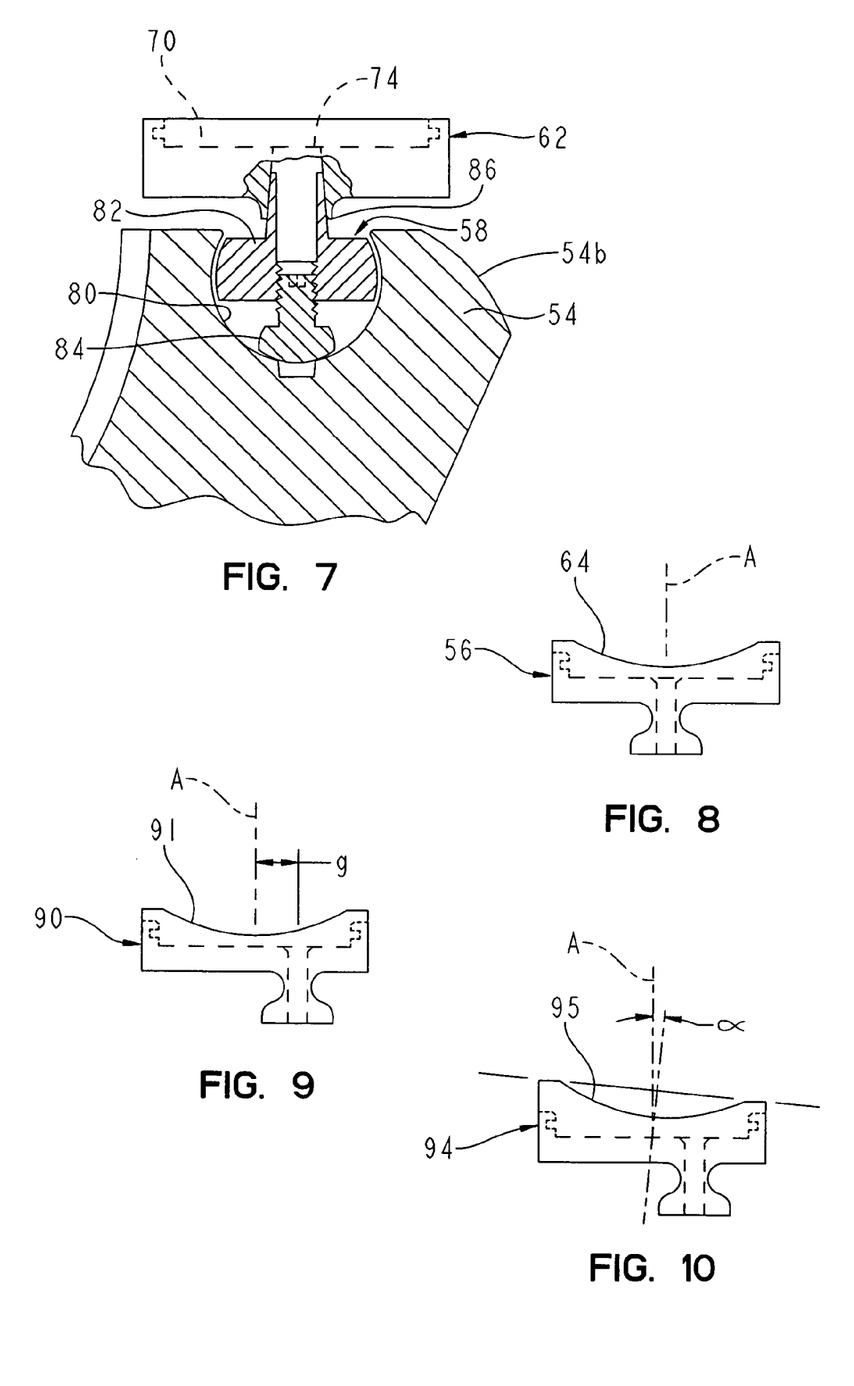
FIG. 7 is an enlarged cross sectional view of an adjustable connection mechanism for use with the humeral component shown in FIG. 4.
FIG. 8 is a side elevational view of a reverse component for use with the humeral component shown in FIG. 4.
FIG. 9 is a side elevational view of an alternative embodiment of a reverse component for use with the humeral component shown in FIG. 4.
FIG. 10 is a side elevational view of yet another embodiment of a reverse component for use with the humeral implant shown in FIG. 4.

Referring still to FIG. 7, it can be seen that the angulation relief 54b allows the bearing support 62 to be pivoted toward the right in FIG. 7 through a significant angle before contacting the proximal portion 54. In the illustration of FIG. 7, the medial relief portion 54a has not been depicted, since the stem 52 can be modified depending upon the degree and direction of angulation desired between the reverse component 56 and the stem 52. However, in the preferred instance, the reverse component 56 can be tilted both medially and laterally, as reflected by the different axis lines A' and A" shown in FIG. 4. It should also be understood that the adjustable connection mechanism 56 can also allow angulation into and out of the plane of the figure for the arrangement shown in FIGS. 4 and 7.

In a further feature of the invention, it is contemplated that the reversible component 56 can be provided in variety of configurations. For instance the reverse component can appear in the different configuration shown in FIGS. 8–10. The reverse component 56 shown in FIG. 8 is generally uniform and symmetric about the central axis A. The bearing surface 64 is uniformly concave, and preferably spherical. On the other hand, as shown in FIG. 9, the centroid of the bearing surface A can be offset from the line of engagement between the reverse component 56 and the proximal portion 54 of the stem 52. Thus, the centroid of the bearing surface 91 of the reverse component 90 shown in FIG. 9 can be offset by a gap G.

Similarly, the angulation of the bearing surface can be modified from perpendicular. Thus, the reverse component 94 can include a bearing surface 95 that is aligned at an offset angle α relative to the centerline of the reverse component. It should be understood that the orientation and configuration of the various bearing surfaces can be modified further still depending upon the particular anatomical requirements for the shoulder prosthesis. For instance, the bearing surface 95 can be shallower or deeper, to mate with a correspondingly configured convex component engaged to the glenoid. In addition, the bearing surface can be offset within the reverse component itself. In this instance, a common bearing support, such as support 62, can be provided for engagement with a variety of different bearing members, such as bearing members 60.

It should be understood that the humeral implant 50 in accordance with the present invention provides a great degree of flexibility intraoperatively. Thus, a surgeon can readily substitute components of the implant as necessary to accommodate the natural anatomy surrounding the shoulder prosthesis. Not only can the orientation of the reverse component be controlled, the configuration of the articulating or bearing surface can also be controlled and modified intraoperatively. One beneficial feature of the invention is that the articulating component, such as reverse components 26 and 56, do not engage the patient's bone. While portions of the components may reside within the envelope defined by the proximal end of the bone, the components are free to move, thus allowing the components to be repositioned or even replaced. This feature makes the present invention particularly suited for trial procedures, as well as for revisions surgeries.

In accordance a surgical method of the present invention, it is contemplated that the humerus is modified to accept the humeral implants described above. In a shoulder arthroplasty, the head of the humerus can be resected to roughly match the implant neck-to-bone shaft angle. The bone canal can be prepared to receive the stem or trial, depending upon the particular surgical procedure. Once the stem is appropriately implanted, a first approach may be to provide a standard convex humeral head prosthesis, engaged to the proximal end of the stem by way of an adjustable connection mechanism, such as the mechanism described above. The humeral head prosthesis can be adjusted and locked in place at an appropriate angle relative to the stem. In many cases, this standard procedure may be sufficient so the standard convex humeral component can remain in place.

However, under certain circumstances the need for a reverse prosthesis may be identified. For instance, if there is joint destruction in the glenoid, soft tissue laxity (such as comprise of the rotator cuff), fracture, or some other instability in the natural shoulder tissue, then the prosthesis can be identified as a candidate for the reverse component. The convex humeral head prosthesis can be removed in anticipation of the addition of a reverse component, such as the components 26 or 56 described above. Since the articular angle is essential to proper functioning of the shoulder prosthesis, additional resection of the proximal portion of the humerus may be required. For instance, additional resection may be necessary if a particularly large articular angle is necessary between the bearing surface of the reverse component and the longitudinal axis of the bone shaft. Once the proximal end of the bone is appropriately prepared, the reverse component can be engaged to the stem and fixed at an appropriate position.

In a preferred method of the invention it is contemplated that the determination of the need for the reverse components would be made intraoperatively during the shoulder arthroplasty procedure. At that point, the particular reverse component can be selected and mounted to the proximal end of the stem by way of an adjustable connection mechanism. However, in some instances, the implantation of the reverse components may be as a result of modification surgery. In a modification procedure, the shoulder implant is modified long after the original arthroplasty procedure has been preformed. Such a modification surgery may arise due to deterioration of the soft tissue surrounding the shoulder prosthesis. In this instance, the modification procedure is greatly simplified by the use of the modular components of the humeral implant, such as the implants 20 and 50. It can be readily appreciated that an existing convex humeral head prosthesis can removed intraoperatively and readily replaced with one of the reverse components described above. This modification can occur without the need for removing the stem of the humeral implant.

In one aspect of the invention, a humeral component kit can be provided. The kit can include a number of stems, such as stem 52, having different lengths and angles at the proximal portion. In addition, a number of support members, such members 62, can be provided that incorporate different offsets and angular orientation. Likewise, a number of bearing members, such as member 60, can also be included in the kit. The number of bearing members can have different bearing surface configurations and orientations. For instance, a kit can include members sufficient to construct each of the reverse components 56, 90, and 94, shown in FIGS. 8–10, as well as other reverse component configurations.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

Figure 11:
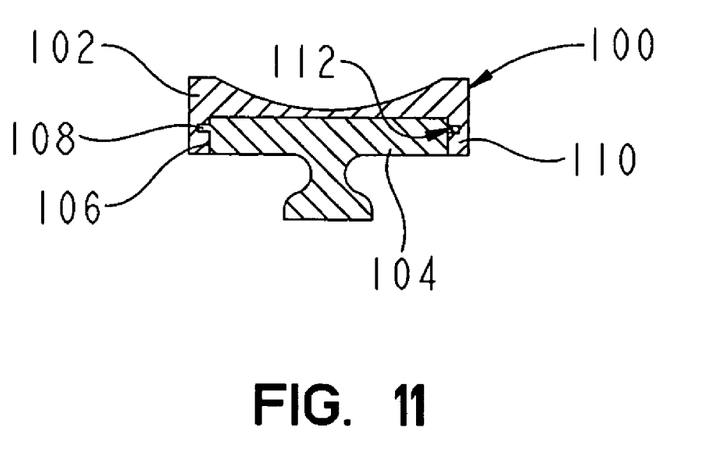
FIG. 11 is a side cross-sectional view of a further embodiment of a reverse component for use with the humeral implant shown in FIG. 4.

For instance, the reverse component 56 is illustrated in FIGS. 4–6 with the bearing member including a hub 66 and the support member including a cavity 70. In an alternative embodiment, the hub and cavity elements can be reversed on the two components, as shown in FIG. 11. A reverse component 100 can include a bearing member 102 and a bearing support 104. The bearing support 104 can defines a hub 106 having a circumferential rib 108 projecting therefrom. The bearing member 102 can include a circumferential skirt 110 that is sized to fit snugly over the hub 106. The skirt defines an interior circumferential recess 112 that is configured for snap-fit engagement with the rib 108.

Figure 12:
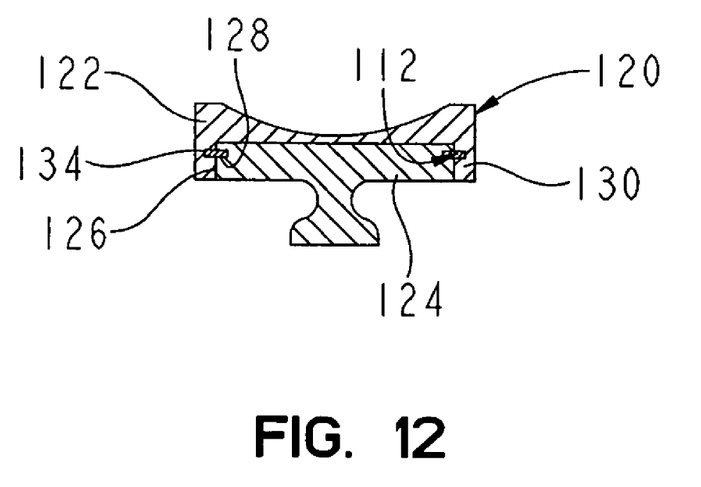
FIG. 12 is a side cross-sectional view of still another embodiment of a reverse component for use with the humeral implant shown in FIG. 4.

As a further alternative, a reverse component 120 can include a bearing member 122 and a bearing support 124, as shown in FIG. 12. Like the embodiment in FIG. 11, the bearing member 122 can include a circumferential skirt 130 that defines an interior circumferential recess 132. The bearing support 124 can also include a hub 126 that fits snugly within the skirt 130. In contrast to the embodiment of FIG. 11, the hub 126 defines a circumferential recess or groove 128 that is coincident with and facing the recess 132 in skirt 130. A snap-ring 134 is provided that snaps into both recesses 128, 132 to hold the two parts of the reverse component 120 together.

With the embodiments shown in FIGS. 11 and 12, the bearing member can be engaged to the bearing support to permit relative rotation between the two parts. For example, the snap-ring 134 can fit within the facing recesses 138, 132 so that the snap-ring only prevents separation of the members but still allows them to rotate relative to each other. In some embodiments, a certain amount of "play" can be incorporated into the snap-ring and recesses so that the members can translate slightly relative to each other. These same degrees of freedom and restriction can be implemented in the embodiments of FIGS. 4–10 as well.

What is claimed is:

1. A humeral component for a shoulder prosthesis comprising:
   a stem configured for implantation within the humerus bone, the stem including a proximal portion configured for positioning in the metaphysis of the humerus;
   an articulating component including a support member and a bearing member removably mounted within said support member so that said articulating component does not engage the humerus bone, said bearing member defining a substantially concave articulating surface; and
   a connection mechanism operable to clamp said articulating component in relation to said proximal portion of said stem at any one of a plurality of angular positions.

2. The humeral component according to claim 1, wherein said connection mechanism is configured to permit connection of said articulating component at variable angles relative to said stem.

3. The humeral component according to claim 1, wherein:
   said support member defines an axis; and
   said connection mechanism is configured to connect said support member along said axis.

4. The humeral component according to claim 3, wherein said concave bearing member defines a central axis projecting from said concave surface, said central axis being substantially aligned with said axis of said support member.

5. The humeral component according to claim 3, wherein said concave bearing member defines a central axis projecting from said concave surface, said central axis being substantially parallel to and offset from said axis of said support member.

6. The humeral component according to claim 3, wherein said concave bearing member defines a central axis projecting from said concave surface, said central axis being non-parallel with said axis of said support member.

7. The humeral component according to claim 1, wherein:
   one of said support member and said bearing member defines a cavity; and
   the other of said support member and said bearing member includes a body sized to fit within said cavity.

8. The humeral component according to claim 7, wherein said cavity and said body define snap-fit features therebetween.

9. The humeral component according to claim 8, wherein said snap-fit features include:
   a first circumferential recess defined on said body;
   a second circumferential recess defined in said cavity coincident with said first recess defined in said body; and
   a snap-ring configured for snap-fit engagement within first and second recesses.

10. The humeral component according to claim 8, wherein said snap-fit features include:
    a circumferential rim defined on said body; and
    a complementary circumferential recess defined in said cavity.

11. The humeral component according to claim 7, wherein said cavity and said body define a press-fit engagement therebetween.

12. The humeral component according to claim 7, wherein said cavity and said body define an anti-rotation feature therebetween to prevent relative rotation between said support member and said bearing member.

13. A humeral component of a shoulder implant, comprising:
    a stem configured for implantation within the humerus bone, said stem including a proximal portion configured for positioning in the metaphysis of the humerus;
    a reverse component kit including a combination of either;
       a support member and a plurality of bearing members;
       a plurality of support members and a bearing member; or
       a plurality of support members and a plurality of bearing members; and
    a connection mechanism, associated with said support members and said proximal portion of said stem, operable to clamp any support member of said reverse component kit in relation to said proximal portion of said stem at any one of a plurality of angular positions,
    wherein each of said bearing members are configured for removable engagement with each of said support members,
    each of said bearing members defines a substantially concave bearing surface, said plurality of support members are mutually differently configured, and
    said plurality of bearing members are mutually differently configured.

14. The humeral component according to claim 13, wherein said plurality of bearing members of said reverse component kit define said concave bearing surface at mutually different angular orientations relative to said support members when said bearing members are engaged to said support members.

15. The humeral component according to claim 13, wherein: each of said support members defines an axis and said connection mechanism is configured to connect said support members along said axis.

16. The humeral component according to claim 15, wherein said plurality of bearing members of said reverse component kit define said concave bearing surface at mutually different angular orientations relative to said axis.

17. The humeral component according to claim 15, wherein said plurality of bearing members of said reverse component kit define said concave bearing surface such that said bearing surface defines a central axis that is offset from said axis of said support members.

18. The humeral component according to claim 13, wherein each of said support members and each of said bearing members define mutually snap-fit features.

19. The humeral component according to claim 18, wherein said mutually snap-fit features include a circumferential rim defined on said body and a complementary circumferential recess defined in said cavity.

20. A humeral prosthesis, comprising:
a humeral implant having a stem configured to be implanted within a humerus;
a bearing support;
a bearing member coupled to said bearing support; and
a connection mechanism operable to secure said bearing support in fixed relation to said humeral implant at any one of a plurality of angular positions,
wherein said humeral implant has a cavity defined in a proximal portion thereof, and
wherein said connection mechanism includes (i) a clamping member positioned within said cavity and having an internally threaded opening defined therein, and (ii) an adjustment screw positioned within said cavity and having an externally threaded member configured to meshingly engage with said internally threaded opening.

21. The humeral prosthesis of claim 20, wherein:
said cavity possesses a truncated spherical configuration, and
said clamping member possesses a partially spherical outer surface.

22. The humeral prosthesis of claim 20, wherein:
said connection mechanism further includes a tapered member,
said bearing support has defined therein a tapered cavity,
said tapered member is configured to be received within said tapered cavity so as to form an interference connection between said bearing support and said tapered member,
said tapered member has a passageway defined therethrough that is axially aligned with said internally threaded opening,
said adjustment screw has a driver orifice configured to receive a driver tool therein, and
said driver orifice is located within said internally threaded opening.

23. A humeral prosthesis, comprising:
a humeral implant having a stem configured to be implanted within a humerus;
a bearing support;
a bearing member coupled to said bearing support; and
a connection mechanism operable to secure said bearing support in fixed relation to said humeral implant at any one of a plurality of angular positions,
wherein said connection mechanism includes a tapered member,
wherein said bearing support has defined therein a tapered cavity,
wherein said tapered member is configured to be received within said tapered cavity so as to form an interference connection between said bearing support and said tapered member.

24. The humeral prosthesis of claim 23, wherein said tapered member has a passageway defined therethrough that is axially aligned with said internally threaded opening.

25. A humeral prosthesis, comprising:
a humeral implant having a stem configured to be implanted within a humerus;
a bearing support;
a bearing member coupled to said bearing support; and
a connection mechanism operable to secure said bearing support in fixed relation to said humeral implant at any one of a plurality of angular positions,
wherein one of said bearing member and said bearing support has defined therein a circumferential engagement recess, and
wherein another of said bearing member and said bearing support includes a circumferential engagement rib configured to be received within said circumferential engagement recess.

26. A humeral prosthesis, comprising:
a humeral implant having a stem configured to be implanted within a humerus, said humeral implant having a receiving space defined in a proximal portion thereof;
a bearing support having defined therein (i) a first cavity, and (ii) a tapered second cavity;
a bearing member positioned within said first cavity; and
a connection mechanism including (i) a clamping member positioned within said receiving space and having an internally threaded opening defined therein, (ii) an adjustment screw positioned within said receiving space and having an externally threaded member configured to meshingly engage with said internally threaded opening, and (iii) a tapered member received in said tapered second cavity in a friction fit manner so as to form a mechanical connection between the bearing support and the tapered member.

27. The humeral prosthesis of claim 26, wherein:
said tapered member has a passageway defined therethrough that is axially aligned with said internally threaded opening,
said adjustment screw has a driver orifice configured to receive a driver tool therein, and
said driver orifice is located within said internally threaded opening.

28. The humeral prosthesis of claim 27, wherein said bearing member covers said tapered second cavity of said bearing support when said bearing member is received within said first cavity of said bearing support.

* * * * *